United States Patent [19]

Dai et al.

[11] Patent Number: 5,698,723

[45] Date of Patent: Dec. 16, 1997

[54] PROCESS FOR THE PREPARATION OF BISTRIPHENYLSILYL CHROMATE

[75] Inventors: Longxiu Dai; Qiwei Duan; Hongbo Ji; Xiaoyuan Wang; Jinqiang Mo; Jinfeng Wang; Hongmei Liu; Xiuqin Li; Jiuhua Chen; Ping Gao, all of Beijing, China

[73] Assignees: China Paeto-Chemical Corporation; Research Institute of Petroleum Processing SINOPEC, both of Beijing, China

[21] Appl. No.: 698,874

[22] Filed: Aug. 16, 1996

[30] Foreign Application Priority Data

Aug. 17, 1995 [CN] China .................. 95109750.4

[51] Int. Cl.$^6$ .................. C07F 11/00; C07F 7/02
[52] U.S. Cl. .................. 556/10; 556/12; 556/57; 502/158
[58] Field of Search .................. 556/10, 12, 57; 502/158

[56] References Cited

U.S. PATENT DOCUMENTS 2,863,891  12/1958  Granchelli et al. .................. 260/429

FOREIGN PATENT DOCUMENTS 689192  6/1977  U.S.S.R. .................. C07F 7/08

OTHER PUBLICATIONS

Excerpt from *Chemical Abstracts*, vol. 90, p. 666, 1979, of Czechoslovakia Patent No. 175,856.

Baker et al., "Bistriphenylsilyl Chromate, Oxidation of Olefins and Use in Ethylene Polymerization" (received Apr. 29, 1969), as published Mar. 1970 in *The Journal of Organic Chemistry*, pp. 774–776.

*Primary Examiner*—Porfirio Nazario-Gonzalez
*Attorney, Agent, or Firm*—Cushman Darby & Cushman Intellectual Property Group of Pillsbury Madison & Sutro LLP

[57] ABSTRACT

Disclosed is a process for the preparation of bistriphenylsilyl chromate, wherein triphenylchlorosilane, potassium dichromate and any one selected from alkali metal oxides, alkali hydroxides and alkali metal carbonates are reacted in, as solvent, a mixture of glacial acetic acid and a hydrocarbon solvent at a certain temperature, whereby bistriphenylsilyl chromate having high purity can be obtained with high yield.

13 Claims, No Drawings

PROCESS FOR THE PREPARATION OF BISTRIPHENYLSILYL CHROMATE

TECHNICAL FIELD

The present invention relates to a process for the preparation of silicon-containing organic compound, and more particularly to a process for the preparation of bistriphenylsilyl chromate.

BACKGROUND OF THE INVENTION

Bistriphenylsilyl chromate is usually used as the catalyst of unsaturated hydrocarbon compound polymerization such as ethylene polymerization. With respect to its synthesis process, early in 1958, U.S. Pat. 7,863,891 disclosed a process wherein bistriphenylsilyl chromate can be obtained with a yield of 85% by reacting triphenylsilanol and chromium trioxide in glacial acetic acid at 50° C. for 10 minutes. L. M. Bakert et al disclosed a process wherein bistriphenylsilyl chromate can be obtained with a yield of about 60% by reacting triphenylsilanol and chromium trioxide in carbon tetrachloride at room temperature for 24 hours [J. Org. Chem., Vol. 85, No. 8, pp. 774–776, March 1970]. The former Czechoslovakia Patent CS 175856 disclosed a process wherein bistriphenylsilyl chromate can be obtained with a yield of 43–71% by reacting triphenylsilanol or triphenylsilyl ether and chromium trioxide in acetonitrile or propyl cyanide. However, the starting material triphenylsilanol used in the above processes is obtained by the hydrolysis of triphenylchlorosilane, so the process for the preparation of bistriphenylsilyl chromate is relatively complicated and the yield thereof is relatively low. The former Soviet Union Patent SU 689192 disclosed a process wherein bistriphenylsilyl chromate can be obtained with a yield of 94% by reacting triphenylchlorosilane and potassium dichromate in glacial acetic acid at 40°–50° C. for 1.5 hours. The reaction equation thereof is as follows:

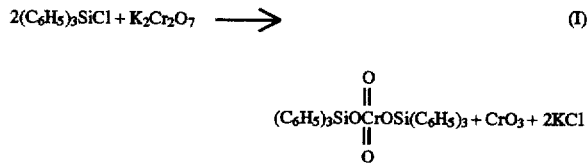

Although said process is relatively simple and the starting materials used are commercially available, the product obtained therefrom has a melting point of only 150°–153° C., demonstrating low purity. If the product with higher purity is desired, further washing or recrystallizing is necessary. However, in this way, the actual yield of the product will be substantially lowered. Moreover, it is known from the reaction equation that the crude product contains relatively much $CrO_3$, which has a slow dissolving rate in glacial acetic acid and water, leading to a higher viscosity of the crude product. As a result, it is difficult to wash and filter the crude product. This is the main cause why the yield of the product is not high.

Accordingly, the object of the present invention is to provide a process with simpler procedure and higher yield and purity of the product, overcoming the drawbacks of the prior art.

SUMMARY OF THE INVENTION

The present invention provides a process for the preparation of bistriphenylsilyl chromate, comprising reacting triphenylchlorosilane, potassium dichromate and any one selected from alkali metal oxides, alkali metal hydroxides and alkali metal carbonates in a mixture of glacial acetic acid and a hydrocarbon solvent at a certain temperature, filtering the resulting reaction mixture to obtain a crude product, then washing the crude product subsequently with water, glacial acetic acid and alkane, and finally drying it to obtain the desired product.

The specific steps and operating conditions of the process according to the present invention are as follows:

(1) reacting triphenylchlorosilane, potassium dichromate and any one selected from alkali metal oxides, alkali metal hydroxides and alkali metal carbonates in a mixture of glacial acetic acid and a hydrocarbon solvent, then filtering the resulting reaction mixture to obtain a crude product, wherein the molar ratio of triphenylchlorosilane to potassium dichromate is 1:0.25–0.80, preferably 1:0.40–0.60, the molar ratio of potassium dichromate to alkali metal oxides, alkali metal hydroxides or alkali metal carbonates is 0.3–1.6:1, preferably 0.6–1.2:1, and the mixing ratio of glacial acetic acid to the hydrocarbon solvent is 0.1–0.9:0.9–0.1 (V/V). The reaction is conducted at a temperature of 20°–100° C., preferably 40°–60° C., for a period of 0.5–12 hours, preferably 2–5 hours; (2) washing the crude product obtained from step (1) subsequently with water, glacial acetic acid and alkane, each of which being used in an amount of 1–10 times, preferably 2–5 times the weight of triphenylchlorosilane; and (3) drying the product obtained from step (2) at a temperature of less than 100° C. for a period of 0.5–4 hours, thereby obtaining the desired product. The starting materials such as triphenylchlorosilane and potassium dichromate are all commercially available.

The hydrocarbon solvent includes alkane, cycloalkane, and aromatic hydrocarbon, with a boiling point of less than 150° C., or a mixture thereof.

The alkali metal oxides include $K_2O$ and $Na_2O$; the alkali metal hydroxides include NaOH and KOH; and the alkali metal carbonates include $K_2CO_3$ and $Na_2CO_3$.

The alkane used in the washing step (2) is preferably hexane.

While the reaction mechanism of the present invention is not known yet, the inventors consider that the addition of alkali metal oxides, alkali metal hydroxides or alkali metal carbonates makes the reaction between triphenylchlorosilane and potassium dichromate more complete. For example, in the case of using KOH, $CrO_3$ formed by the reaction of equation (I) reacts with KOH to form $K_2CrO_4$, which further reacts with triphenylchlorosilane to obtain the product; or triphenylchlorosilane is hydrolyzed by KOH into $(C_6H_5)_3SiOH$ which easily reacts with $CrO_3$, thereby obtaining the product. In this way, the starting materials can be fully utilized and the pollutant requiring post-treatment can be reduced. Moreover, the use of a mixture of glacial acetic acid and a hydrocarbon solvent as solvent results in a decreased surface tension of the reactants, thus it is much easier to filter and wash the product, and the product having higher purity can be obtained without recrystallization. For example, when the process of the invention is used, a product having a melting point of 154–161 can be obtained with a yield of 90–97.4%.

BEST MODE OF THE INVENTION

The present invention will be explained in detail by the following examples.

EXAMPLE 1

30 g triphenylchlorosilane, 13 g potassium dichromate, 3 g potassium hydroxide, 60 ml glacial acetic acid and 80 ml hexane are added into a 500 ml three-neck flask equipped with a stirrer and a reflux condenser. The reaction mixture is stirred at 50°–60° C. for 5 hours, then filtered. The resulting solid is washed subsequently with 140 ml water, 70 ml glacial acetic acid and 70 ml hexane and filtered under reduced pressure, and finally dried in an oven under vacuum, to obtain 31.2 g product with a yield of 97.4%. The differential scanning calorimetry (DSC) analysis indicates that the product has a melting point of 154° C.

Elementary analysis (using carbon & hydrogen element analyser for C and H; and chemical analysis method in accordance with GB223.11-82 for chromium, respectively) of $C_{36}H_{30}O_4Si_2Cr$:

Calculated: C 68.12%, H 4.76%, Cr 8.19%; Found: C65.40%, H 4.50%, Cr 8.20%.

EXAMPLE 2

The same procedure as used in Example 1 is followed, except that a mixture of 60 ml glacial acetic acid and 60 ml hexane is used as solvent, and the amount of hexane used for washing is 60 ml instead of 70 ml, to obtain 29.4 g product. The resultant product has a melting point of 156° C. with a yield of 91%.

Elementary analysis of $C_{36}H_{30}O_4Si_2Cr$: Found: C67.10%, H 4.50%, Cr8.00%.

EXAMPLE 3

The same procedure as used in Example 1 is followed, except that the amount of potassium dichromate used is 8.4 g instead of 13 g, 3.5 g potassium carbonate is used instead of 3 g potassium hydroxide and 200 ml water, 110 ml glacial acetic acid and 120 ml hexane are used for washing, to obtain 29.6 g product. The resultant product has a melting point of 159° C. with a yield of 91.6%.

Elementary analysis of $C_{36}H_{30}O_4Si_2Cr$: Found: C 66.1%, H 4.5%.

EXAMPLE 4

The same procedure as used in Example 1 is followed, except that a mixture of 60 ml glacial acetic acid and 80 ml cyclohexane is used as solvent, to obtain 29.6 g product. The resultant product has a melting, point of 156° C. with a yield of 91.6%.

Elementary analysis of $C_{36}H_{30}O_4Si_2Cr$: Found: C 66.41%, H 4.62%.

EXAMPLE 5

The same procedure as used in Example 1 is followed, except that 2.1 g sodium hydroxide is used instead of 3 g potassium hydroxide, to obtain 30.8 g product. The resultant product has a melting point of 153° C. with a yield of 95.4%.

Elementary analysis of $C_{36}H_{30}O_4Si_2Cr$: Found: C 65.80%, H 4.52%.

EXAMPLE 6

The same procedure as used in Example 1 is followed, except that a mixture of 60 ml glacial acetic acid and 80 ml benzene is used as solvent, to obtain 31.4 g product. The resultant product has a melting point of 154° C. with a yield of 7.4%.

Elementary analysis of $C_{36}H_{30}O_4Si_2Cr$: Found: C 66.22%, H 4.67%.

EXAMPLE 7

The same procedure as used in Example 1 is followed, except that 70 ml petroleum ether having a dry point of 120° C. is used for washing instead of hexane, to obtain 29.4 g product. The resultant product has a melting point of 154° C. with a yield of 91%.

Elementary analysis of $C_{36}H_{30}O_4Si_2Cr$: Found: C 65.80%, H 4.56%.

EXAMPLE 8

30 g triphenylchlorosilane, 13 g potassium dichromate, 2.1 g sodium hydroxide, 60 ml glacial acetic acid and 80 ml hexane are charged into a 500 ml three-neck flask equipped with a stirrer and a reflux condenser. The reaction mixture is stirred at 20° C. for 0.5 hour, then the temperature of the reaction mixture is raised to 80° C., over 3 hours. After the reaction mixture is stirred at 80° C. for 0.5 hour, the heating is stopped. The reaction mixture is stirred for additional 3.5 hours, then filtered. The resulting solid is washed subsequently with 100 ml water, 60 ml glacial acetic acid and 80 ml hexane and filtered under reduced pressure, and finally dried in an oven under vacuum, to obtain 29.4 g product having a melting point of 154° C. with a yield of 91%.

Elementary analysis: Found: C 65.5%, H 4.49%.

Comparative Example 1

In this comparative example, bistriphenylsilyl chromate is prepared in accordance with the process of SU 689192 except that reaction time is 5 hours instead of 1.5 hours.

30 g triphenylchlorosilane, 7.5 g potassium dichromate and 120 ml glacial acetic acid are charged into a 500 ml three-neck flask equipped with a stirrer and a reflux condenser. The reaction mixture is stirred at 40°–50° C. for 5 hours, then filtered. The resulting solid is washed subsequently with 240 ml water, 240 ml glacial acetic acid and 240 ml hexane, and then dried in an oven under vacuum, to obtain 20.2 g product having a melting point of 151° C. with a yield of 66%.

Elementary analysis: Found: C 69.46%, H 4.85, Cr 7.56%.

It is evident from the above results that the product obtained has very low purity with low yield even when the reaction time is 3.5 hours longer than that of example 1 in SU 689192.

Comparative Example 2

The same procedure as used in Comparative example 1 is followed, except that the amount of potassium dichromate used is 12 g instead of 7.5 g. 26.5 g product having a melting point of 149° C. is obtained with a yield of 86%.

Elementary analysis: Found: C 57.80%, H 4.10%.

This comparative example indicates that, when the process of SU 689192 is used, the yield and the purity of the product are still low even if potassium dichromate is used in excess of 60%.

We claim:

1. A process for the preparation of bistriphenylsilyl chromate, comprising the steps of:
    (1) reacting triphenylchlorosilane, potassium dichromate and any one selected from alkali metal oxides, alkali metal hydroxides and alkali metal carbonates in a mixture of glacial acetic acid and a hydrocarbon solvent at 20–100 for 0.5–12 hours, then filtering the resulting reaction mixture to obtain a crude product, wherein the molar ratio of triphenylchlorosilane to potassium dichromate is 1:0.25–0.80, the molar ratio of potassium dichromate to alkali metal oxides, alkali metal hydroxides or alkali metal carbonates is 0.3–1.6:1;

(2) washing the crude product obtained from step (1) subsequently with water, glacial acetic acid and alkane; and (3) drying the product obtained from step (2).

2. A process for the preparation of bistriphenylsilyl chromate according to claim 1, wherein the molar ratio of triphenylchlorosilane to potassium dichromate is 1:0.40–0.60.

3. A process for the preparation of bistriphenylsilyl chromate according to claim 1, wherein the molar ratio of potassium dichromate to alkali metal oxides, alkali metal hydroxides or alkali metal carbonates is 0.6–1.2:1.

4. A process for the preparation of bistriphenylsilyl chromate according to claim 1, wherein said alkali metal oxides are $K_2O$ and $Na_2O$.

5. A process for the preparation of bistriphenylsilyl chromate according to claim 1, wherein said alkali metal hydroxides are KOH and NaOH.

6. A process for the preparation of bistriphenylsilyl chromate according to claim 1, wherein said alkali metal carbonates are $K_2CO_3$ and $Na_2CO_3$.

7. A process for the preparation of bistriphenylsilyl chromate according to claim 1, wherein each of water, glacial acetic acid and alkane used in said step (2) is in an amount of 1–10 times the weight of triphenylchlorosilane.

8. A process for the preparation of bistriphenylsilyl chromate according to claim 1, wherein said step (3) is carried out at a temperature of less than 100° C. for a period of 0.5–4 hours.

9. A process for the preparation of bistriphenylsilyl chromate according to claim 1, wherein said hydrocarbon solvent used in said step (1) is alkane, cycloalkane, or aromatic hydrocarbon, with a boiling point of less than 150° C., or a mixture thereof.

10. A process for the preparation of bistriphenylsilyl chromate according to claim 1, wherein the reaction temperature in said step (1) is 40°–60° C.

11. A process for the preparation of bistriphenylsilyl chromate according to claim 1, wherein the reaction time in said step (1) is 2–5 hours.

12. A process for the preparation of bistriphenylsilyl chromate according to claim 1, wherein said alkane used in said step (2) is hexane.

13. A process for the preparation of bistriphenylsilyl chromate according to claim 1, wherein the mixing ratio of glacial acetic acid to the hydrocarbon solvent in said mixture is 0.1–0.9:0.9–0.1 (V/V).

* * * * *